United States Patent [19]

Bildstein et al.

[11] 4,110,365

[45] Aug. 29, 1978

[54] PROCESS FOR THE MANUFACTURE OF NAPHTHALENE-MONOSULFONIC ACIDS

[75] Inventors: Siegfried Bildstein; Rudolf Lademann; Siegfried Pietzsch, all of Kelkheim, Taunus; Georg Schaeffer, Hofheim, Taunus, all of Fed. Rep. of Germany

[73] Assignee: Hoechst Aktiengesellschaft, Frankfurt am Main, Fed. Rep. of Germany

[21] Appl. No.: 590,498

[22] Filed: Jun. 26, 1975

Related U.S. Application Data

[63] Continuation of Ser. No. 417,755, Nov. 21, 1973, abandoned.

[30] Foreign Application Priority Data

Nov. 24, 1972 [DE] Fed. Rep. of Germany ....... 2257676
Jan. 20, 1973 [DE] Fed. Rep. of Germany ....... 2302869

[51] Int. Cl.$^2$ ............................................. C07C 143/24
[52] U.S. Cl. ................................................. 260/505 C
[58] Field of Search ......................... 260/505 C, 505 S

[56] References Cited

U.S. PATENT DOCUMENTS

| | | | |
|---|---|---|---|
| 1,332,203 | 3/1920 | Dennis | 260/505 |
| 2,884,463 | 4/1959 | Heller | 260/505 |
| 3,198,849 | 8/1965 | Ballestra | 260/505 |

Primary Examiner—A. Siegel
Attorney, Agent, or Firm—Curtis, Morris & Safford

[57] ABSTRACT

Preparation of naphthalene-monosulfonic acids from naphthalene and sulfuric acid at elevated temperatures.

8 Claims, No Drawings

PROCESS FOR THE MANUFACTURE OF NAPHTHALENE-MONOSULFONIC ACIDS

This is a continuation of application Ser. No. 417,755, filed Nov. 21, 1973, now abandoned.

This invention relates to a process for the manufacture of naphthalene-monosulfonic acids by continuously reacting naphthalene and sulfuric acid at elevated temperature.

It is known to produce naphthalene-sulfonic acids by reacting naphthalene with sulfuric acid. Depending on the reaction conditions mono- and polysulfonic acids are formed in this reaction and the proportion of generally unwanted polysulfonic acids in the reaction product increase with the $SO_3$ concentration, the reaction temperature and the time of reaction.

One the two isomeric forms of naphthalene-monosulfonic acid the α-acid is preferably formed at low temperature while the β-acid is preferably formed at higher temperature.

In industry naphthalene-monosulfonic acids are produced in a discontinuous process by reacting naphthalene batchwise with sulfuric acid, for the production of the α-acid at a temperature of up to about 50° C., for the preparation of the β-acid at a 160° to 165° C. (cf. BIOS Final Report No. 1152, Item No. 22). Especially in the higher temperature range, it is necessary first to mix the naphthalene with sulfuric acid at a temperature which is lower than the sulfonating temperature in order that the formation of disulfonic acids be kept as low as possible.

In a Russian publication (J. angew. Chem./USSR-/volume 36, page 1793 (1963) it has been proposed to reduce the speed of sulfonation and the oxidizing action of sulfuric acid with formation of tarry by-products by adding at least 6% by weight of sodium sulfate, calculated on the naphthalene used to such an extent that the preliminary mixing of the reactants at a temperature below the sulfonating temperature can be dispensed with.

The author holds that this simplification permits to develop a continuous process. The addition of sodium sulfate in the indicated minimum amount is, however, unbearable in a large scale process.

It has also been proposed to carry out the sulfonation of naphthalene with sulfuric acid continuously in a vertical tube reactor (Chem. Průmysl, volume 15, No. 11, page 641 (1965). In this process the conversion of naphthalene is, however, much too low, owing to the increased hydrolysis of the naphthalene-monosulfonic acids by the reaction water in the high layer of the reaction mixture. By prolongation of the reaction period and increase of the amount of sulfuric acid the naphthalene conversion can be increased, but simultaneously the content of disulfonic acids rises to more than 15% by weight. A satisfactory conversion of naphthalene can be obtained by carrying out the reaction in a trough shaped reactor in which the layer thickness of the sulfonation mixture is at most a few centimeters, so that a rapid removal of the reaction water is ensured. In this process the reactants must be pre-mixed in a separate vessel and it is quite obvious that such an open system is unsuitable for industrial use as considerable amounts of naphthalene would pass into the air.

In view of the aforesaid state of the art an expert was led to believe that in the manufacture of naphthalene-monosulfonic acids by sulfonation of naphthalene at elevated temperature, according to the experiences gained with discontinuous processes, naphthalene and sulfuric acid had to be pre-mixed at a temperature below the reaction temperature in order to keep as low as possible the proportion of disulfonic acids and the formation of resinous by-products. This prejudice is a result from the cited publications teaching that the addition of concentrated sulfuric acid to the reaction mixture having a temperature of 163° C. involves an increased polysulfonation and, due to its oxidizing action, the formation of tarry by-products, which may be avoided by the addition of at least 6% by weight of sodium sulfate, which considerably reduces, however, the sulfonation speed.

The present invention provides a process for the manufacture of naphthalene-monosulfonic acids by continuously reacting naphthalene and sulfuric acid at elevated temperature, which comprises intensely mixing the reaction components at a temperature in the range of from 140° to 185° C. until a homogeneous phase is formed and terminating the reaction in this homogeneous phase.

When operating in this manner the disadvantages of the known processes with regard to the formation of undesired by-products and losses of yield are substantially avoided. By carrying out the reaction at a temperature in the range of from 140° to 185° C. mainly β-naphthalene-monosulfonic acid is formed besides small amounts of α-naphthalene-monosulfonic acids. The ratio of alpha- to beta-sulfonic acid is generally determined by the reaction temperature, the reaction period, the concentration of sulfuric acid and the water content in the reaction mixture. The process of the invention is preferably carried out at a temperature of from 150° and 170° C., more preferably 160° to 165° C. The reaction takes place at atmospheric pressure or under reduced pressure, the speed of water evaporation increasing with increasing fall in pressure. The pressure should, however, only be reduced to such an extent that the boiling point of the naphthalene at the given reaction temperature is not reached and it remains substantially available in the reaction mixture for the sulfonating reaction. With consideration of this requirement any reduction of pressure is possible, the range of from about 100 to about 600 torr being preferred. Especially good results are obtained in a pressure range of from 200 to 500 torr.

The reaction period or the average residence time of the sulfonation mixture in the reactor may amount up to 10 hours and depends on the reaction temperature, the mixing proportion of the reaction components sulfuric acid and naphthalene and possibly on the elimination of the reaction water in the course of the reaction. At 163° C. and with an excess of sulfuric acid of 22 mole % the residence time may be in the range of approximately 1 to 4 hours with a proportion of alpha- to beta-naphthalene-monosulfonic acid of about 0.18 to 0.05. The time of intense mixing of the reactants in the reactor until a homogeneous phase is formed is likewise determined by the reaction temperature and the molar proportion of the reactants, it is in the range of from a few minutes to half an hour. After formation of the homogeneous phase the reaction mixture can leave the zone of intense mixing without demixing with separation of the phases when the mixing intensity subsides. The reaction is suitably terminated in a zone connected with the mixing zone. The reaction speed depends not only on the temperature and the sulfuric acid concentration but also on the water content of the reaction mixture. The zone of intense mixing and the reaction zone may have the same or a different design.

A certain minimum period of time is required until the homogeneous phase is formed and it has been found that the reaction of naphthalene and sulfuric acid does not take place under optimum conditions as long as the homogeneous phase has not formed substantially or completely.

According to a preferred embodiment of the invention the intense mixing of the reaction components is performed in a zone in which the homogeneous phase of the reactants has substantially or completely formed. During the continuous reaction the homogeneous phase is continuously produced from the reactants and solubilizes immediately the supplied reaction components naphthalene and sulfuric acid.

By homogeneous phase in the sense of the invention a solution or an emulsion is understood which, after leaving the mixing zone, does not show any sign of demixing under the reaction conditions. The residence time of the reactants in the mixing vessel necessary for the formation of a homogeneous phase is determined by the mixing proportion of the components, the temperature and the water content of the reaction mixture; it is, for example in the range of from a few minutes to half an hour. To obtain a homogeneous phase of sulfuric acid and naphthalene about 9 minutes of intense mixing are required with a molar proportion of 1.2 at a temperature of 160° C. Into the homogeneous sulfonation mixture obtained the two reactants are introduced in dosed quantities, simultaneously but separately from each other and continuously at a rate warranting the required minimum residence time of the reactants in the mixing vessel, i.e. for the formation or maintenance of the homogeneous phase. With sufficient intense mixing, for example stirring, the starting components are immediately and continuously dissolved in the reaction mixture whereby the homogeneity is maintained and an optimum distribution ensured. Only at the points of introduction of the reactants into the homogeneous sulfonation mixture a minor turbidity may be observed. After the required residence time, the homogeneous reaction mixture leaves the mixing zone without separating into phases, in spite of subsiding mixing intensity, so that the reaction can be terminated in a following reaction zone. The mixing zone and the reaction zone may have the same or different construction. In the case of a sufficiently large mixing vessel a special reaction zone may even be dispensed with.

By partially or completely removing the reaction water from the reaction mixture the yield of monosulfonic acids, calculated on the sulfuric acid used, is increased, the reaction period is reduced and the formation of α-naphthalene-monosulfonic acid is favored. Hence, it is preferable to remove the reaction water completely or partially from the reactor, advantageously by distillation under reduced pressure. According to a particularly preferred embodiment of the process of the invention the reaction is performed with addition of hydrocarbons forming azeotropic mixtures with water, which can then be distilled off. The hydrocarbon may be recycled. Suitable hydrocarbons are those which form azeotropic mixtures with water having a boiling point below the reaction temperature of the sulfonation mixture and which are inert under the reaction conditions, for example hydrocarbons of the aliphatic, alicyclic, aromatic, or araliphatic series, as well as halogen containing hydrocarbons or mixtures of these compounds. Especially preferred are heptane, cyclohexane, fractions of gasoline hydrocarbons, kerosene fractions, fractionated hydrocarbon mixtures originating from petroleum distillation and boiling from about 60° C. upward; hexane, octane, nonane, ethylene chloride, carbon tetrachloride, and chloroform. Heptane, for example, which boils at 98° C., forms with water an azeotrope distilling at 80° C. at atmospheric pressure.

The device used for carrying out the process of the invention may consist of one or several series connected vessels with stirrer (cascade) provided with reflux condensers. The agitator vessels may be provided with fractionating columns for azeotropes so that the reaction water can be distilled off as an azeotrope, for example after the addition of heptane, whereby the conversion and the space-time-yield are improved. Alternatively, the sulfonation can be performed under pressure in a closed apparatus comprising vessels with stirrers, fractionating columns and vacuum receivers for the distillation of the reaction water and valve-like charging means for the starting materials and means to withdraw the reaction product. The process can also be performed in a flow tube with equipments analogous to that of the cascade.

In the process of the invention premixing of the reactants at a temperature below the sulfonation temperature is not required as can be seen from the following table enumerating experiments in which naphthalene and sulfuric acid were premixed at different temperatures below the sulfonation temperature of 163° C. in a vessel connected in series with a cascade of vessels with stirrers, which do not indicate any dependence of the yield of naphthalene-monosulfuric acids on the mixing temperature. A prerequisite is, however, that the starting components are intensely mixed as rapidly as possible until a homogeneous phase is formed which does no longer demix. Such a homogeneous phase can be rapidly produced, for example by intensely stirring in the reactor cascade or by producing a turbulent flow in a tube-shaped reactor, for example by the installation of baffle plates. The intense mixing may also be brought about by the use of vibro-mixers or ultrasonics.

As compared with the known processes for the manufacture of naphthalene-monosulfonic acids, especially the discontinuous industrial processes, the continuous process of the present invention is characterized, above all, by the fact that the monosulfonic acids obtained are free from noticeable proportions of disulfonic acids, so that the usual expensive purification processes can be dispensed with. Owing to the very high yields of naphthalene-monosulfonic acids, calculated on the sulfuric acid used, the process of the invention is very economic and constitutes an important progress of the state of the art.

The naphthalene-monosulfonic acids obtained by the process of the invention are valuable intermediates, for example for the manufacture of dyes, insecticides, fungicides and auxiliaries for rubber industry.

The following examples illustrate the invention. Experimental data and the results of the examples are summarized in the following table.

EXAMPLE 1

Four agitator flasks having a total filling volume of 2 liters and joined in cascade were used as continuous sulfonating apparatus. Molten naphthalene and 96% sulfuric acid of room temperature were metered in by laboratory piston pumps.

During the course of 601 minutes 3.820 g of naphthalene and 3.755 g of sulfuric acid of 96% strength were pumped into the first flask. The average residence time of the sulfonation mixture in the cascade at 163° C. was 195 minutes during which 75% of the sulfuric acid were reacted.

A sample taken from the last flask at the end of the cascade had a content of disulfonic acid of less than 1% by weight.

EXAMPLE 2

In an agitator flask an excess of 22 mole % of 96% sulfuric acid were added to molten naphthalene. After a reaction period of 120 minutes at 163° C., during which 76% of the sulfuric acid were reacted, the discontinuously prepared sulfonation mixture contained 2% by weight of disulfonic acids.

EXAMPLE 3

The reaction was carried out in the same apparatus as used in Example 1, with the exception that a mixing vessel having a filling volume of 0.1 l was connected in series.

During the course of 617 minutes 4,663 g of naphthalene and 4,585 g of 96% sulfuric acid were pumped into the mixing vessel at 130° C. The average residence time of the reaction mixture in the mixing vessel at 130° C. until a homogeneous phase had formed was 12 minutes. In the connected cascade the average residence time was 166 minutes at 163° C. The conversion of sulfuric acid amounted to 74%.

A sample taken from the last flask at the end of the reaction period had a disulfonic acid content of less than 1% by weight.

EXAMPLE 4

The same continuous apparatus as in Example 3 was used. During the course of 619 minutes 4,691 g of naphthalene and 4,600 g of 96% sulfuric acid were pumped into the mixing vessel at 163° C. The average residence time of the sulfonation mixture in the cascade and the mixing vessel was 175 minutes at 163° C., during which time 73% of the sulfuric acid were reacted.

A sample taken from the last reaction flask at the end of the reaction period had a disulfonic acid content of less than 1% by weight.

EXAMPLE 5

In a flask with stirrer provided with water separator 3.0 moles of 96% sulfuric acid and 20 g of heptane were added to 3.3 moles of molten napthalene. After 40 minutes at 160° C., during which water and heptane were distilled of as azeotrope and the heptane was recycled, 96% of the sulfuric acid were reacted.

After removal of the heptane the discontinuously prepared sulfonation mixture contained 2% by weight of disulfonic acids.

EXAMPLE 6

The reaction was carried out as described in Example 5. After 30 minutes at 170° C. and with 20 g of heptane, 95% of the sulfuric acid were reacted.

The discontinuously prepared sulfonation mixture contained 2% by weight of disulfonic acids.

EXAMPLE 7

The reaction was carried out as described in Example 5. After 80 minutes at 140° C. with 40 g of heptane, 94 g of the sulfuric acid were reacted.

After removal of the heptane the discontinuously prepared sulfonation mixture contained 2% by weight of disulfonic acids.

EXAMPLE 8

The continuous apparatus of Example 3 was used with the exception that each reaction flask was additionally provided with a water separator.

During an operation period of 10 hours naphthalene and 96% sulfuric acid were pumped at 160° C. into the mixing vessel in a molar ratio of 1.1. Simultaneously, the amount of heptane necessary to eliminate the water as azeotrope was added in analogy to Example 5. The average residence time of the sulfonation mixture in the cascade and the mixing vessel was 91 minutes at 160° C., during which period water and heptane were distilled off as azeotrope and the heptane was recycled. 95% of the sulfuric acid were reacted.

A sample taken from the last reaction flask at the end of the reaction period had a disulfonic acid content of less than 1% by weight after removal of the heptane.

EXAMPLE 9

The reaction was carried out as described in Example 8. During an operation period of 10 hours naphthalene and 96% sulfuric acid were pumped into the mixing vessel at 170° C. in a molar ratio of 1.1. Simultaneously, the amount of heptane necessary to eliminate the reaction water as azeotrope was added in analogy to Example 5.

The average residence time of the sulfonation mixture in the cascade and mixing vessel was 67 minutes at 170° C. and 94% of the sulfuric acid were reacted.

A sample taken from the last reaction flask at the end of the reaction period had a disulfonic acid content of less than 1% by weight after the removal of the heptane.

EXAMPLE 10

The reaction was carried out as described in Example 8. During an operation period of 10 hours naphthalene and 96% sulfuric acid were pumped into the mixing vessel at 140° C. in a molar ratio of 1.1. Simultaneously, the amount of heptane necessary to eliminate the water as azeotrope was added to the reaction mixture. The average residence time of the sulfonation mixture in the cascade and the mixing vessel was 155 minutes at 140° C. 94% of the sulfuric acid were reacted.

A sample taken from the last reaction flask at the end of the reaction had a disulfonic acid content of less than 1% by weight after the removal of the heptane.

EXAMPLE 11

In a flask with stirrer provided with distilling column and vacuum receiver 3.0 moles of 96% sulfuric acid were added to 4.2 moles of molten naphthalene. After 60 minutes at 163° C., during which water and 0.3 mole of naphthalene distilled over at reduced pressure (400 torr), 97% of the sulfuric acid had reacted.

The discontinuously prepared sulfonation mixture contained 2% by weight of disulfonic acids.

EXAMPLE 12

The cascade of Example 1 was used which was connected in series with a mixing vessel having a filling volume of 0.3 l. Each reaction flask was provided with a distilling column and vacuum receiver.

During an operation period of 10 hours naphthalene and 96% sulfuric acid were pumped at 163° C. into the mixing vessel in a molar ratio of 1.4. The average residence time of the sulfonation mixture in the cascade and the mixing vessel was 120 minutes at 163° C., during which reaction water and a little naphthalene distilled off under reduced pressure (400 torr) and 96% of the sulfuric acid were reacted.

A sample taken from the last reaction flask at the end of the reaction period had a disulfonic acid content of less than 1% by weight.

EXAMPLES 13 and 14

The reaction was carried out as described in Example 1, however with shorter residence times. Details and the results are listed in the following table.

EXAMPLES 15 and 16

The reaction was carried out as described in Example 3, however at higher mixing temperatures. Details and the results are listed in the following table.

EXAMPLE 17

As continuous sulfonation apparatus a mixing vessel with stirrer having a filling volume of 0.1 l and a connected cascade of 4 flasks with stirrers having a total filling volume of 2 l were used.

During an operation period of 619 minutes 4,691 g of molten naphthalene of about 100° C. and 4,600 g of 96% sulfuric acid having room temperature (molar proportion sulfuric acid to naphthalene 1.22) were pumped into the mixing vessel heated at 163° C. The average residence time of the two reaction components or the homogeneous sulfonation mixture, respectively, was 9 minutes. The reaction mixture passed by an overflow into the cascade wherein the reaction was completed at 163° C. The average residence time of the reaction mixture in the cascade of agitator flasks was 166 minutes. 73% of the sulfuric acid were reacted.

A sample taken from the last flask at the end of the reaction period contained less than 1% by weight of disulfonic acid.

EXAMPLE 18

As continuous sulfonation apparatus a mixing vessel with stirrer having a filling volume of 0.1 l and 5 series connected U-shaped reaction tubes having a total filling volume of 2 l were used.

During an operation period of 611 minutes, 4,621 g of molten naphthalene of about 100° C. and 4,530 g of 96% sulfuric acid having room temperature (molar proportion of sulfuric acid to naphthalene = 1.23) were pumped into the mixing vessel heated at 163° C. The average residence time of the two reaction components or the homogeneous sulfonation mixture, respectively, was 9 minutes. From the mixing vessel the reaction mixture passed into the tube shaped reactor through an overflow. In the reactor the reaction was completed at 163° C. at an average residence time of 173 minutes. 76% of the sulfuric acid were reacted.

The sample taken at the outlet of the tube reactor had a disulfonic acid content of less than 1% by weight.

TABLE

| Ex. No. | temp. °C in mixing[1] vessel | No. of stages in cascade[3] | $H_2SO_4$/naphthalene (moles) | operation period (min) | residence time (min)[4] | reaction temp. °C | pressure (torr) | hydrocarbon entrainer | $H_2SO_4$ conversion % | disulfonic-acid content wt %[5] |
|---|---|---|---|---|---|---|---|---|---|---|
| 2 | — | discont. | 1.22 | — | 120 | 163 | 760 | — | 76 | 2 |
| 5 | — | " | 0.91 | — | 40 | 160 | 760 | heptane | 96 | 2 |
| 6 | — | " | 0.91 | — | 30 | 170 | 760 | heptane | 95 | 2 |
| 7 | — | " | 0.91 | — | 80 | 140 | 760 | heptane | 94 | 2 |
| 11 | — | " | 0.71 | — | 60 | 163 | 400 | — | 97 | 2 |
| 13 | — | 4 | 1.22 | 607 | 88 | 163 | 760 | — | 64 | <1 |
| 14 | — | 4 | 1.22 | 594 | 164 | 163 | 760 | — | 73 | <1 |
| 1 | — | 4 | 1.23 | 601 | 195 | 163 | 760 | — | 75 | <1 |
| 3 | 130 | 4 | 1.23 | 617 | 178 | 163 | 760 | — | 74 | <1 |
| 15 | 140 | 4 | 1.22 | 614 | 178 | 163 | 760 | — | 74 | <1 |
| 16 | 150 | 4 | 1.23 | 473 | 165 | 163 | 760 | — | 73 | <1 |
| 8 | 160 | 4 | 0.91 | 600 | 91 | 160 | 760 | heptane | 95 | <1 |
| 9 | 170 | 4 | 0.91 | 600 | 67 | 170 | 760 | heptane | 94 | <1 |
| 10 | 140 | 4 | 0.91 | 600 | 155 | 140 | 760 | heptane | 94 | <1 |
| 4 | 163 | 4 | 1.22 | 619 | 175 | 163 | 760 | — | 73 | <1 |
| 12 | 163[2] | 4 | 0.71 | 600 | 120 | 163 | 400 | — | 96 | <1 |
| 17 | 163 | 4 | 1.22 | 619 | 166 | 163 | 760 | — | 73 | <1 |
| 18 | 163 | 5 | 1.23 | 611 | 173 | 163 | 760 | — | 76 | <1 |

[1] filling volume 0.1 l
[2] filling volume 0.3 l
[3] filling volume 4 × 0.5 l
[4] ≈ reaction period
[5] isolated by column chromatography and determined by titration

What is claimed is:

1. A process for the manufacture of naphthalene-monosulfonic acids by reacting naphthalene and sulfuric acid at elevated temperature, which comprises: intensely mixing a portion of the said reaction components at a temperature in the range of from 140° to 185° C. until a homogeneous phase has formed; and thereafter introducing further portions of said reaction components into said homogeneous phase and completing the reaction of said components in said homogeneous phase.

2. The process of claim 1, wherein the reaction components are intensely mixed in a zone already containing the homogeneous phase formed from the reaction components.

3. The process of claim 1, wherein the reaction is completed in a zone following the mixing zone.

4. The process of claim 1, wherein the reaction is performed in a reactor cascade.

5. The process of claim 1, wherein the reaction is carried out in a tube reactor.

6. The process of claim 1, wherein the reaction water is completely or partially separated.

7. The process of claim 6, wherein the reaction water is separated by addition of an azeotrope-forming hydrocarbon.

8. The process of claim 6, wherein the reaction water is eliminated under reduced pressure.

* * * * *